(12) United States Patent
Baggett

(10) Patent No.: US 7,691,091 B1
(45) Date of Patent: Apr. 6, 2010

(54) COVER FOR A URINE DRAINAGE BAG

(76) Inventor: Sue Baggett, P.O. Box 263, Pamplico, SC (US) 29583

( * ) Notice: Subject to any disclaimer, the term of this patent is extended or adjusted under 35 U.S.C. 154(b) by 771 days.

(21) Appl. No.: 10/262,715

(22) Filed: Oct. 3, 2002

(51) Int. Cl.
*A61M 1/00* (2006.01)

(52) U.S. Cl. .................................. 604/317; 604/327

(58) Field of Classification Search ......... 604/327–332, 604/343, 353; 2/46–51, 104, 88, 207
See application file for complete search history.

(56) References Cited

U.S. PATENT DOCUMENTS

| | | | | |
|---|---|---|---|---|
| 2,857,599 | A | * | 10/1958 | Wallace ............................ 2/48 |
| 4,025,961 | A | * | 5/1977 | Peters .............................. 2/88 |
| 4,087,864 | A | * | 5/1978 | LaBove et al. .................. 2/102 |
| 4,122,851 | A | | 10/1978 | Grossner |
| 4,173,979 | A | | 11/1979 | Odis |
| 4,280,227 | A | * | 7/1981 | Brock .............................. 2/88 |
| 4,331,148 | A | | 5/1982 | Steer et al. |
| 4,401,245 | A | * | 8/1983 | Zills ........................ 224/148.3 |
| 4,519,797 | A | | 5/1985 | Hall |
| 4,526,280 | A | * | 7/1985 | Taylor ........................ 215/395 |
| 4,606,736 | A | | 8/1986 | Van De Weghe |
| 4,804,367 | A | * | 2/1989 | Smith et al. .................. 604/113 |
| 4,874,387 | A | | 10/1989 | Boone |
| 4,924,528 | A | * | 5/1990 | Trombetti-Dickens ......... 2/104 |
| D313,693 | S | * | 1/1991 | Coates ......................... D2/861 |
| D316,602 | S | | 4/1991 | Dungan et al. |
| 5,034,999 | A | * | 7/1991 | Lubbers ......................... 2/104 |
| D328,953 | S | | 8/1992 | Garcia |
| D331,460 | S | | 12/1992 | Mulder |
| 5,248,308 | A | | 9/1993 | von Emster |
| D368,000 | S | * | 3/1996 | Mazza et al. ................. D7/625 |
| 5,607,412 | A | | 3/1997 | Brown |
| 5,843,054 | A | | 12/1998 | Honig |
| 6,015,261 | A | * | 1/2000 | Barone ......................... 416/62 |
| D432,232 | S | | 10/2000 | Molina |
| 6,186,989 | B1 | | 2/2001 | Horie |
| D438,616 | S | | 3/2001 | Williams |
| 6,406,463 | B1 | * | 6/2002 | Brown ......................... 604/349 |
| D470,586 | S | * | 2/2003 | Felstet ....................... D24/128 |

* cited by examiner

*Primary Examiner*—Michele Kidwell
(74) *Attorney, Agent, or Firm*—B. Craig Killough; Ernest B. Lipscomb, III

(57) ABSTRACT

A urine drainage bag cover covers and hides the contents of a urine drainage bag, but is easily manipulated, so that the fluid level in the urine drainage bag may be easily ascertained by attendants.

8 Claims, 2 Drawing Sheets

COVER FOR A URINE DRAINAGE BAG

FIELD OF THE INVENTION

This invention is a cover for a urine drainage bag.

BACKGROUND OF THE INVENTION

Urine drainage bags are in common use in hospitals, nursing homes and similar care facilities. Urine drainage bags collect urine from patients who are bed ridden, or are otherwise not sufficiently ambulatory to use the toilet. Urine drainage bags are connected by means of a catheter to the patient, and as the patient urinates, urine flows through a conduit and into the urine drainage bag. Urine drainage bags are typically hung, or mounted in some manner, to the side of the patient's bed. Typically, the outer layer of the urine drainage bag is transparent, so that attendants may easily and conveniently check the level of the bag. When the level of urine in the urine drainage bag rises to a certain level, the bag is emptied or replaced. The urine drainage bag is typically placed in a conspicuous location, so that checking the bag is easy for attendants. The likelihood of the bag becoming overfilled is thereby reduced.

Urine drainage bags are unsightly. The presence of these bags is frequently an embarrassment to the patient or nursing home resident, who suffers a loss of dignity from the conspicuous placement of the urine drainage bag.

A need exists for a cover that will hide the contents of the urine drainage bag, but will, at the same time, allow the urine drainage bag to be positioned in a conspicuous manner. The cover should also allow the urine drainage bag to be easily checked by attendants to determine the fluid level in the urine drainage bag.

SUMMARY OF THE PRESENT INVENTION

The present invention is a urine drainage bag cover. The urine drainage bag cover covers and hides the contents of a urine drainage bag, but is easily manipulated, so that the fluid level in the urine drainage bag may be easily ascertained by attendants.

DETAILED DESCRIPTION OF THE INVENTION

Figure 1:
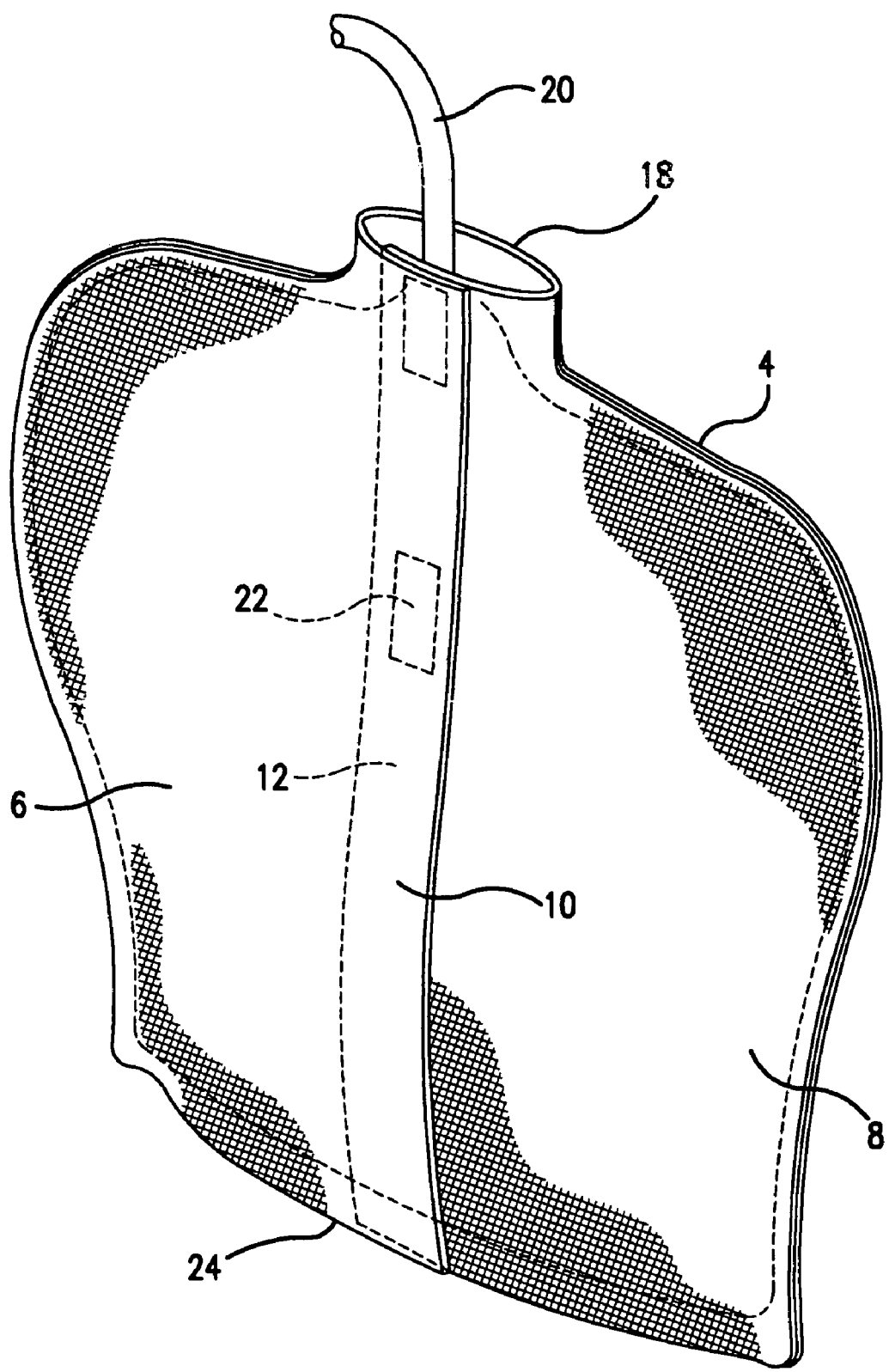
FIG. 1 is a perspective view of a preferred embodiment of the urine drainage bag cover as it covers a urine drainage bag.

The urine drainage bag cover of the present invention is formed of a sheet of flexible material, such as a blend of polyester and cotton. The sheet has a sufficient height and sufficient width to completely surround a urine drainage bag 2. The sheet has a back 4, a left front side 6, and a right front side 8. The left front side and the right front side overlap, and meet to form an opening where a generally vertical edge 10 of the left front side meets a generally vertical edge 12 of the right front side. The sheet may be formed of a single piece of fabric, or it may be formed of two or more pieces of fabric that are connected, such as by sewing or gluing. For example, the back may be formed of one piece of fabric while each of the left front side and the right front side are formed of additional and separate pieces of fabric. Alternatively, the back and front of the cover may be a unitary sheet of fabric.

The fabric sheet as formed in a preferred embodiment has a left shoulder 14 and a right shoulder 16, with the shoulder formed where the front of the cover joins the corresponding back portion of the cover. The shoulders slope generally downward from the neck 18 of the device to the outside of the shoulders, and have an arcuate shape from the top of the shoulders to the sides of the cover. The bottom of the cover has a width that is less than the widest point of the cover at the top of the cover near the shoulders.

Near the top and center of the cover a neck 18 is formed. The urine drainage bag will have a conduit 20 that typically extends into the bag through a top and center of the bag. The conduit extends through an opening in the cover at the top and the center of the cover, which is defined herein as the neck. The neck extends generally upwardly from the shoulders. The neck hides an upper portion of the drainage bag cover.

Figure 2:
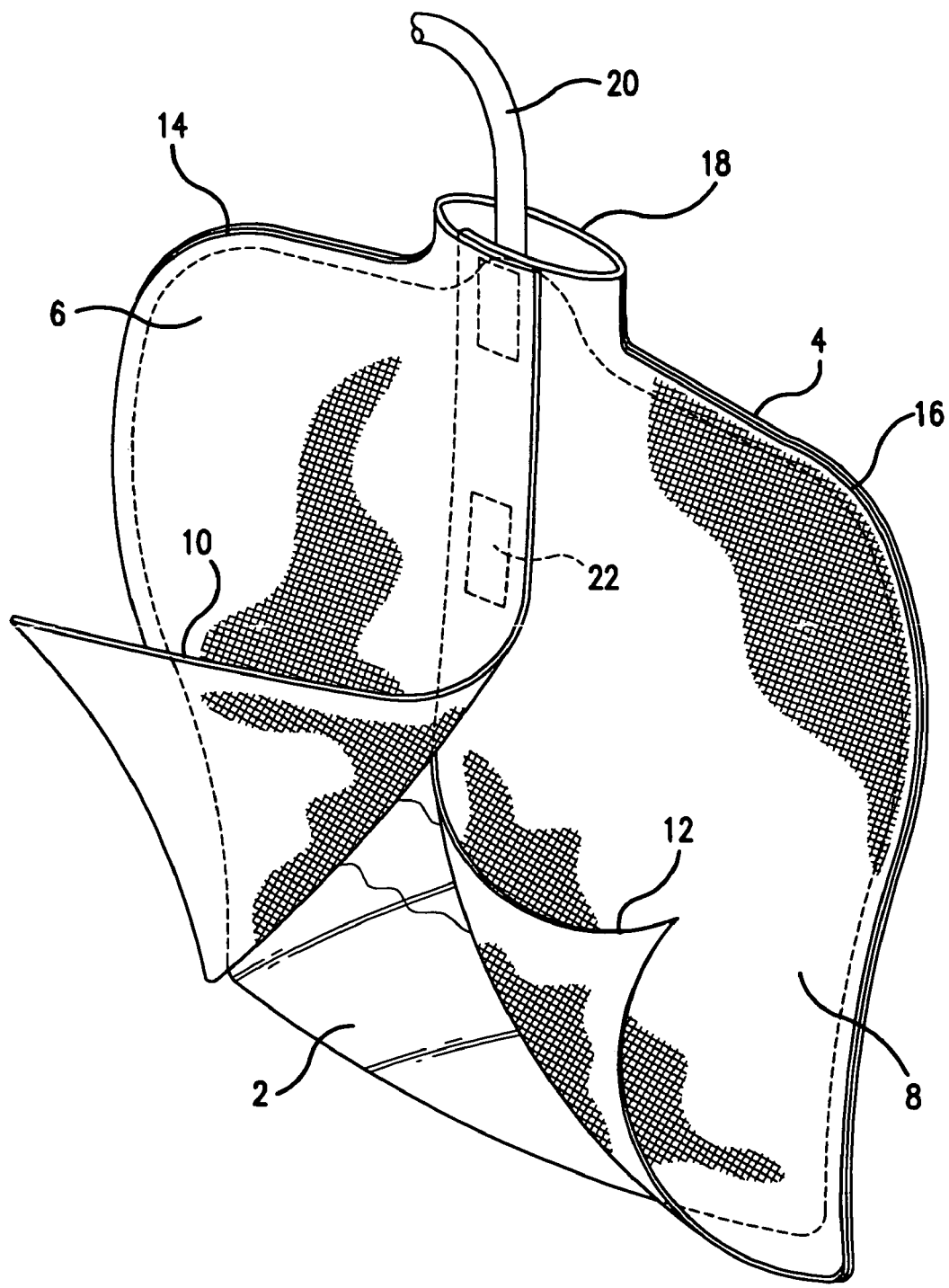
FIG. 2 is a perspective view of the urine drainage bag of FIG. 1, showing the cover opened for checking of the fluid level within the urine drainage bag.

Attachment means are provided where the generally vertical portion of the left front of the cover joins the generally vertical portion of the right front of the cover. Attachment may be provided by a button, snap, clasp or similar device. The preferred means of attachment is hook and loop material 22, such as VELCRO®. It is material to the invention that there be no attachment of the cover where the left front side joins the right front side beyond ⅓ of the length from the top of the cover and along the opening. As is demonstrated by FIG. 2, the lower portion of the opening formed where the generally vertical edge of the left front side joins the generally vertical edge of the right front side is not attached along the lower ⅔ of the length thereof, so that the cover may be easily opened by an attendant to check the fluid level of the urine drainage bag. The device is constructed so that an attendant need not manipulate an attachment device to check the fluid level in the bag. Hook and loop material positioned near an upper portion of the opening will adequately retain the cover in place, while permitting easy checking of the fluid level in the urine drainage bag. The use of hook and loop material also allows the cover to be easily removed and fitted when it is necessary to empty or replace the urine drainage bag.

The device has an opening in the neck for the conduit. The neck also has an opening in the front that extends from opening between the left front side and the right front side. There is also an opening in the bottom of the device to facilitate opening of the cover; in other words, the back and the front of the device are not attached at any point along a lower edge 24 of the cover, except precisely at the left and right side of the cover. The device has no opening on the sides, such as where the front and back of the cover meet, nor are there openings in the back of the device.

The invention claimed is:

1. A urine drainage bag having a cover, comprising:
   a urine drainage bag, said urine drainage bag comprising a conduit extending from a top portion of said urine drainage bag;
   a covering for said urine drainage bag, said covering formed of a sheet, said covering having a sufficient height and a sufficient width to substantially surround said urine drainage bag, said covering having an opening formed therein where a first generally vertical edge of said covering meets an opposite generally vertical edge of said covering, and wherein a top portion of said covering has a neck opening formed therein, and wherein a shoulder extends downwardly from each side of said neck opening, and wherein an interior of said shoulder rests upon said top portion of said urine drainage bag on each side of said neck opening and supports said covering, and wherein said neck opening communicates with said opening and said conduit extends through said neck opening;

a fastener that is positioned in an upper portion of said opening, wherein said fastener connects said first generally vertical edge of said sheet to said opposite generally vertical edge of said sheet at an upper portion of said first generally vertical edge of said sheet and an upper portion of said opposite generally vertical edge of said sheet;

wherein a lower portion of said opening of said sheet is formed where a lower portion of said generally vertical edge meets a lower portion of said opposite generally vertical edge, and said lower portion of said generally vertical edge is not connected to said lower portion of said opposite generally vertical edge of said sheet, and wherein said lower opening of said sheet covers a portion of said urine drainage bag when said lower portion of said opening is closed, and reveals a portion of said urine drainage bag and a level of contents of said urine drainage bag when said lower portion of said opening is opened by separating said lower portion of said generally vertical edge from said opposite generally vertical edge.

2. A urine drainage bag having a cover as described in claim 1, wherein said shoulder comprises an arcuate shoulder formed on a left side of an upper portion thereof that slopes downwardly from a neck of said cover, and an arcuate shoulder formed on a right side of an upper portion thereof that slopes downwardly from said neck of said cover.

3. A urine drainage bag having a cover as described in claim 1, wherein said neck opening extends generally upwardly from said shoulder on either side of said neck opening and near a center of said upper portion of said cover, wherein a portion of said opening extends through said neck opening on a front side of said neck opening.

4. A urine drainage bag having a cover as described in claim 1, wherein said fastener is present in said neck opening.

5. A urine drainage bag having a cover as described in claim 1, wherein said fastener that connects said first generally vertical edge of said sheet to said opposite generally vertical edge of said sheet in an upper portion of said first generally vertical edge of said sheet and an upper portion of said opposite generally vertical edge of said sheet does not extend below one third of a length of said opening measured from a top edge of said opening.

6. A urine drainage bag having a cover as described in claim 1, wherein said fastener is formed of hook and loop material.

7. A urine drainage bag having a cover as described in claim 1, wherein said neck opening is formed by an annular ring that extends generally vertically upwardly from said shoulder on either side of said neck opening and about the entire circumference and near a center of said upper portion of said cover, wherein a portion of said opening extends through said neck opening on a front side of said neck opening.

8. A urine drainage bag having a cover as described in claim 1, wherein said fastener is positioned in said neck opening and above where said shoulder joins said neck opening.

* * * * *